(12) United States Patent
Boone et al.

(10) Patent No.: US 6,927,858 B2
(45) Date of Patent: Aug. 9, 2005

(54) APPARATUS AND METHOD FOR MEASURING THE VOLUME OF AN OBJECT

(75) Inventors: John M. Boone, Sacramento, CA (US); Philip D. Schneider, Sacramento, CA (US)

(73) Assignee: The Regents of the University of California, Oakland, CA (US)

( * ) Notice: Subject to any disclaimer, the term of this patent is extended or adjusted under 35 U.S.C. 154(b) by 204 days.

(21) Appl. No.: 10/185,598

(22) Filed: Jun. 26, 2002

(65) Prior Publication Data

US 2004/0001204 A1 Jan. 1, 2004

(51) Int. Cl.[7] .......................... G01N 21/00; A61B 5/103
(52) U.S. Cl. ....................................... 356/437; 600/587
(58) Field of Search ........................... 356/437; 600/587

(56) References Cited

U.S. PATENT DOCUMENTS 5,331,409 A * 7/1994 Thurtell et al. ............. 356/437

OTHER PUBLICATIONS

D.M. Mikes, B.A. Cha, C.L.Dym, J. Baumgaertner, A.G. Hartzog, A. D. Tacey, M. R. Calabria, *Bioelectrical Impedance Analysis Revisited*, [Comment In: Lymphology. Sep. 2000; 33 (3) :137–7 UI: 20470908]. Lymphology 32, 157–165 (1999).

J.T. Kakuda, M. Stuntz, V. Trivedi, S.R. Klein, and H.I. Vargas, *Objective Assessment of Axillary Morbidity In Breast Cancer Treatment*, Am. Surg. 65, 995–998 (1999).

L.I. Valentin and W.H. Valentin, *Comparative Study of Different Venous Reflux Duplex Quantitation Parameters*, Angiology 50, 721–728 (1999).

L.H. Gerber, *A Review of Measures of Lymphedema*, Cancer 83, 2803–2804 1998.

S.R. Harris, M.R. Hugl, I.A. Olivotto, and M. Levine, *Clinical Practice Guidelines For The Care and Treatment Of Breast Cancer*:11. Lymphedema, Steering Committee for Clinical Practice Guidelines for the Care and Treatment of Breast Cancer., CMAJ. Jan. 23, 2001; 164. (2) :191–9. 164, 191–199 (2001).

M.A. Kosir, C.Rymal, P.Koppolu, L. Hryniuk, L.Darga, W.Du, V. Rice, D. Mood, S. Shakoor, W. Wang, J. Bedoyan, A. Aref, L. Biernat, and L. Northouse, *Surgical outcomes after breast cancer surgety*:measuring acute lyphedema, J.Surg.Res. Feb. 2001.;95. (2) :147–151 95, 147–151(2001).

M. Duff, A. D. Hill, G. McGreal, S. Walsh, E.W. McDermott, and N.J. O'Higgins, Prospective Evaluation Of the Morbidity of Axillary Clearance For Breast Cancer, Br.J. Surg. Jan. 2001.; 88. (1) :114–7.88, 114–117 (2001).

A.W. Stanton, C. Badger, and J. Sitzia, *Non–invasive Assessment of the Lymphedematous Limb*, Lymphology 2000. Sep.:33(3) :122–35.33 122–135 (2000).

(Continued)

*Primary Examiner*—Zandra V. Smith
(74) *Attorney, Agent, or Firm*—Audrey A. Millemann; Weintraub Genshlea Chediak Sproul

(57) ABSTRACT

An apparatus and method for measuring the volume of an object with particular application to measuring the volume changes in the limbs of patients suffering from lymphedema. The apparatus is comprised of a cylinder having a measurement chamber for placing a patient's limb. The chamber is sealed and a gas having known light absorption characteristics is injected into the chamber and mixed with the ambient air therein. A reference laser beam is projected through ambient air to a photocell on the cylinder and the optical absorption value of the reference beam is recorded. A second laser beam is projected through the air-gas mixture of the measurement chamber and the light absorption value is recorded. The ratio of the absorption value of the reference beam to the second laser beam is determined and this value is used to calculated a value which is proportional to gas concentration, which in turn is proportional to the volume of an object placed within the cylinder.

73 Claims, 3 Drawing Sheets

OTHER PUBLICATIONS

W. Svensson, D.M.Glass, D. Bradley, and A. M. Peters, *Measurement of Lyphatic Function with Technetium–99m–labelled Polyolonal immunoglobulin*, Eur. J. Nucl. Med. 26, 504–510 (1999).

A.W. Stanton, J.W. Northfield, B. Holroyd, P.S. Mortimer, and J.R. Levick, *Validation of an Optoelectronic Limb Volumeter (Perometer)*, Lymphology 30, 77–97 (1997).

B.H. Cornish, I.H. Bunce, L.C. Ward L.O. Jones, and B.J. Thomas, *Bioelectrical impedance for monitoring the Efficacy of Lymphoedema Treatment Programmes*, Breast Cancer Res. Treat. 38, 169–176 (1996).

V. Logan, *Incidence and Prevalence of Lyphmoedema: a Literature Review*. J.Clin.Nure. 4 213–219 (1995).

S. P. Pani, P. Vanamail, and J. Yuvaraj, *Limb Circumference Measurement For Recording Edema Volume in Patients With Filarial Lyphedema*, Lymphology 28, 57–63 (1995).

Saskin R.J. Thiadens, R.N. *Lymphedema Awareness Before, During and After Breast Cancer Surgery*, Newletter Article Reprint vol. 10, No. 3 Jul.–Sep. 1998.

Pumps are Not the Answer for Lymphedema National Lymphedema Network Jul./Sep. 2001.

Website: http://www.womanpersonalhealth.com/lymphedema.htm, The Womans Personal Health Resource—Lyphedema Support and . . . Mar. 13, 2002.

* cited by examiner

APPARATUS AND METHOD FOR MEASURING THE VOLUME OF AN OBJECT

1. FIELD OF INVENTION

This invention pertains to an apparatus for monitoring and measuring the volume of body limbs. The invention can also be used in industrial applications for measuring the volume of inanimate objects.

2. BACKGROUND OF INVENTION

Human breast cancer often spreads to the lymph nodes of a patient, thereby requiring the removal of one or more of the linguinal or axillary lymph nodes. This type of lymph node removal as a component of breast cancer surgery is very common. After surgery involving lymph node removal, a large number of breast cancer patients experience a condition known as lymphedema. Lymphedema occurs as both an acute and chronic condition in which significant and persistent swelling associated with an abnormal accumulation of protein-rich fluid is experienced in the affected areas, such as the arms. This swelling can cause extreme pain in the arms and cosmetic issues, which affect the quality of life experienced by lymphedema sufferers.

Among the two million breast cancer survivors in the United States, it is conservatively estimated that 20–40% will develop chronic lymphedema within their lifetimes. The extensive nature of this disease makes the development of devices which monitor and treat lymphedema, a necessity, if the quality of life of its sufferers is to be improved. Lymphedema is most commonly treated by subjecting the patient's arms to pressure cuff treatment. The pressure cuff device essentially wrings the protein-rich fluid from the patient's arms, thereby reducing swelling. Another form of treatment is for the patient to wear body-constricting garments such as arm tubes constructed from tight-weave material which constricts the arm, thereby maintaining the reduced volume and shape of the arm.

The types of devices which are used in medical facilities to monitor and measure lymphedema include that disclosed in French Patent No. FR2682279 by Cauzot et al. The Cauzot patent describes a device which uses a sheath to fit over a patient's limb, the sheath is then filled with a compressible or incompressible fluid. A volume computer measures the increase in volume of a patient's arm due to swelling. Further, this device is used as a pressure cuff in pressure therapy. A drawback to the Cauzot device is that it is required to be hooked to a nearby fluid source or else a fluid source must be transported along with the device, thereby limiting its transportability and location of use.

U.S. Pat. No. 5,948,977 by Siconolfi describes a displacement volumometer for measuring a whole body or a single limb. A person places his entire body or a single limb within a large air bag and the bag is compressed to two positions and compared against a constant air pressure when the bag is empty and fully inflated. The person's body or limb volume is then calculated based upon the changes in volume according to Boyle's law. The large size of the air bag associated with this device makes it impractical from a portability standpoint as well.

The "Mercury Plethysmograph" Publication describes estimating changes in body or limb volume by using an apparatus comprised of an inflated cuff coupled around a limb that is coupled to air flow and pressure transducers. The purpose of the apparatus is to measure fluid perfusion into a limb. While transportable, this device requires some significant time spent in coupling and positioning the cuff around the limb, inflating it, and then allowing enough time for an accurate reading to be taken. Also, the inflatable cuff is more prone to wear and puncture, thereby limiting its operational life.

A need therefore exists for a portable and durable apparatus for accurately measuring lymphedema in patients. Further, it would be desirable for such a device to quickly take lymphedema measurements with as little patient interference as possible.

The foregoing discussion reflects the state of the art which the inventor is aware, and is tendered with a view toward discharging the inventor's acknowledged duty of candor in disclosing information which may be pertinent with regards to the patentability of the present invention. It is respectfully stipulated, however, that the disclosed information does not teach or render obvious, singly or when considered in combination, the inventor's claimed invention.

SUMMARY OF THE INVENTION

The invention is an apparatus for measuring the volume of an object using differences in laser light absorption occurring between a laser beam traveling through ambient air versus a laser beam traveling through an ambient air and gas mixture. This invention calculates the volume of an object by requiring that an object be placed inside of a rigid housing having a hollow measurement chamber. A known quantity of gas is injected into the chamber which mixes with ambient air in the chamber. A laser beam is projected through the air/gas mixture to a light receiver, such as a photocell. Further, another laser beam is projected through pure ambient air, also to a photocell receiver. A ratio between light absorbed by the respective photocells, is calculated which is used to arrive at a value that is proportional to gas concentration. Gas concentration is in turn proportional to object volume and thereby the volumes of objects within the measurement chamber can be readily determined.

In a preferred embodiment of the invention the apparatus is adapted for measuring the volume of a human limb for purposes of quantifying the progression of lymphedema. The rigid housing is a cylinder with a measurement chamber for placing a patient's limb, the cylinder having a laser measuring system, as previously noted, for measuring the volume of the patient's limb within the cylinder. The patient's arm is measured by the apparatus prior to surgery to get a volume reference, and is then compared against the volume of the patient's arm post-surgery, to determine the progression of lymphedema, if any. The laser measuring system allows the patient's arm to be measured very quickly. The rigid cylinder is placed upon an elevated stand which is attached to a wheeled platform containing any associated peripheral components of the device, thereby allowing it to operate in a fully self-contained manner. The wheeled platform allows the apparatus to be freely transportable and the relatively compact size of the apparatus allows it to be easily moved from room to room in a medical facility, as it is needed.

Another embodiment of the invention has the apparatus being both a lymphedema quantifying apparatus and a lymphedema treating apparatus. Here, the cylinder housing would also be a pressure chamber which could be pressurized for purposes of reducing the volume of a human limb, thereby treating lymphedema. After each successive pressurization, the volume of a limb could be re-measured to determine if treatment has occurred.

The following objects and advantages will be revealed from the detailed disclosure of the invention:

It is an object of the invention to provide an apparatus for measuring the volume of objects both animate and inanimate.

It is a further object of the invention to provide an apparatus for measuring the volume of human limbs for purposes of quantifying the progression of lymphedema or other maladies.

Still another object of the invention is to provide an apparatus for both measuring and treating lymphedema.

It is another object of the invention to describe a method for using the apparatus to measure the volume of an object, such as a human limb.

Further objects and advantages of the invention will be brought out in the following portions of the specification, wherein the detailed description is for the purpose of fully disclosing preferred embodiments of the invention, without placing limitations thereon.

BRIEF DESCRIPTION OF THE DRAWINGS

The invention will be more fully understood by reference to the following drawings which are for illustrative purposes only.

DESCRIPTION OF THE PREFERRED EMBODIMENTS

Figure 1:
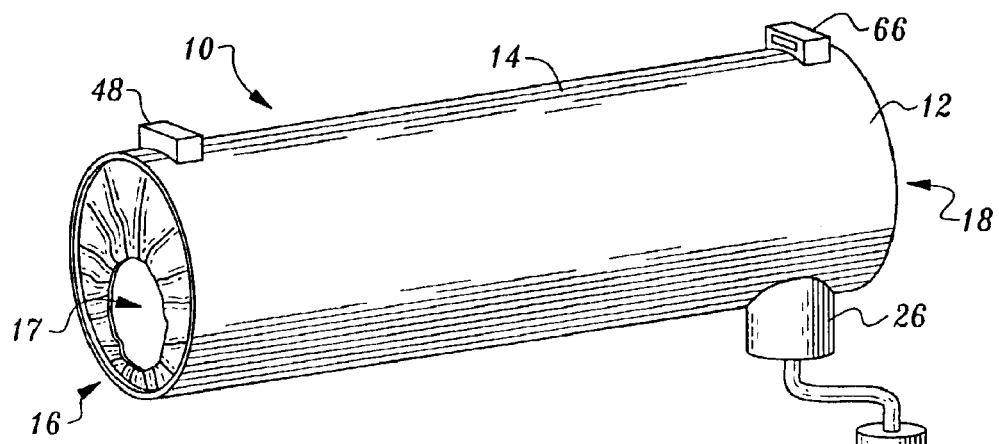
FIG. 1 is an elevated perspective view of a first embodiment of the inventive apparatus for quantifying lymphedema.

For illustrative purposes, FIG. 1 shows the basic inventive apparatus 10 for measuring the volume of objects. The apparatus is comprised of a rigid housing having a hollow chamber, which, in FIG. 1, is comprised of a hollow cylinder 12 with a rigid wall 14. Cylinder 12 has first 16 and second 18 ends, with first end having an opening 17 for placing objects inside of the hollow chamber.

Figure 2:
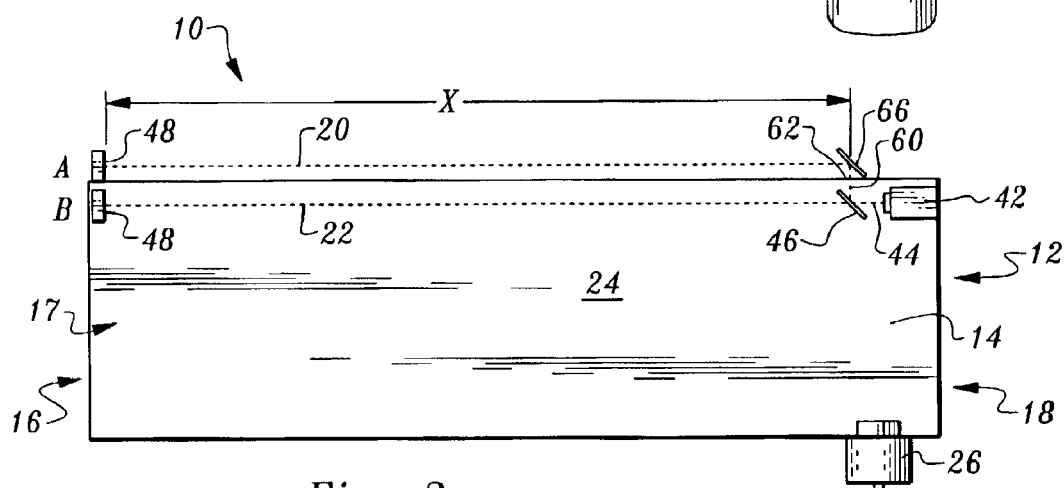
FIG. 2 is a cutaway side view of a first embodiment of the inventive apparatus.

Still referring to FIG. 1 and also to FIG. 2, the remaining components of the basic apparatus 10 can be examined. FIG. 2 is a cutaway view showing the internal components of a first preferred embodiment of the apparatus 10. The inventive apparatus uses two laser beams to determine the volume of an object. A first laser beam 20 is projected down the length of the cylinder 12, through ambient air, and serves as a reference beam. A second laser beam 22 is projected inside of the cylinder 12, also lengthwise, and through an environment of ambient air mixed with a known quantity of gas. With an object present in the measurement chamber 24 of cylinder 12, increased optical absorption occurs due to increased gas concentration when compared with an empty cylinder 12 having an equivalent quantity of introduced gas. Likewise, a larger object will increase gas concentration, and therefore cause a higher optical absorption of second beam 22, when compared with a smaller object. This relation of gas concentration is proportional to object volume, as will be further discussed herein.

As shown in the figures, a known quantity of gas is introduced into the cylinder through a gas valve 26. Gas valve is coupled to a gas source 28, a portable gas bottle being preferred, to keep the apparatus entirely self-contained, but a stationary source of gas could be used as well. The gas that is chosen must have an optical absorption spectrum which absorbs noticeably at certain light wavelengths emitted by a chosen laser or other light source. The wavelengths absorbed by the gas can be in any portion of the light spectrum for purposes of the inventive apparatus 10. The inert gasses meet the requirements of the invention, but the invention is in no way limited to these. Also, as an alternative to the measuring gas, an aerosol can be introduced into the measurement chamber to act as a measuring medium. Colored smoke is just such an exemplary aerosol.

Figure 3:
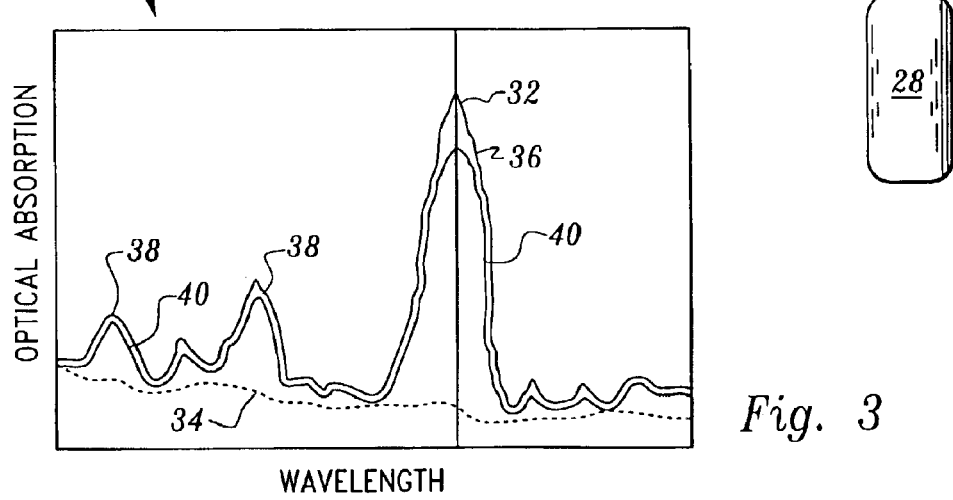
FIG. 3 is graph of a hypothetical gas where the gas is selected for its ability to absorb certain wavelengths of light emitted from a laser.

As shown in FIG. 3, a graph 30 of the optical absorption curve 32 of a hypothetical pure gas is shown along with a curve 34 for pure ambient air. The peaks in the gas curve 32 show the wavelength values on the light spectrum at which the gas absorbs the most. The gas that is chosen can absorb light in any portion of the light spectrum, including visible, ultraviolet, and infrared and the point of absorption on the light spectrum makes no difference in the calculation of the ratio A/B, as long as A and B are measured at the same wavelength. The pure gas curve 32 shown has a large peak 36 and several smaller peaks 38. A mixture of a known quantity of the hypothetical gas and ambient air (as would occur in the measurement chamber) would show an absorption curve 40 having similarly placed, smaller peaks, located between the pure gas and ambient air curves of FIG. 3. To illustrate the relation of the curves, as larger and larger objects are placed within the measurement chamber 24 of the apparatus 10, the curve 40 would move closer to curve 32, due to increases in gas concentration within the chamber.

Again referring to FIGS. 1 and 2, the first and second laser beams 20, 22 emanate from a laser beam projector 42. A continuous beam projector is preferred, but a pulsed beam projector could be used. A laser diode operates well as a projector 42. The invention also contemplates the use of non-laser light sources. Laser light sources are monochromatic, however other light sources while typically being polychromatic can be converted to monochromatic light with an appropriate optical transmission filter. However, if no filter is used, then the apparatus must include multiple detectors which are individually sensitive to specific wavelengths of light whether they be visible, infrared, or ultraviolet light sources. The light source that is selected must emit light at wavelengths which correspond with the absorption bands (peaks) of the measuring gas.

Still referring to FIGS. 1 and 2, a single laser beam projector 42 projects a beam 44 which is split into first and second beams 20, 22 through use of a partially silvered mirror 46, prism, or other beam splitter. The partially silvered mirror 46 would ideally deflect fifty per cent (50%) of the projected beam 44 to a second deflecting mirror 66 and this beam becomes first beam 20 having path length X. The remaining fifty per cent (50%) of the projected beam 44 that is not deflected passes through the partially silvered mirror 46 and becomes second beam 22, which travels along path length X, which ends at photocell light detector 48. The path length X of first and second beams is preferably identical so that accurate ratios of absorption values A and B can be obtained, in a manner discussed in further detail, below. However, different path lengths of first and second beam can be used, as long as the apparatus is properly calibrated to take these different path lengths into account.

The first and second laser beams are received by a photocell 48, such as a photodiode or phototransistor. The apparatus 10 has associated electronics 50 (see FIG. 6) which interpret the beams 20, 22 received by the photocells 48, the electronics 50 also being capable of auto-calibrating the apparatus. For example, as the photocells absorb the laser light, they relay laser beam intensity data to an analog to digital converter which then relays the digital data to a computer. A power supply powers various components including the computer. The computer also receives input from a pressure transducer 52 which senses barometric pressure and a digital thermometer 54 for sensing temperature. The electronics 50 may further be linked to a TV monitor screen output 53 and a printer output 55 so that the user can keep a record of the volume measurement of an object.

Alternatively, while the drawings illustrate each of the two beams 20, 22 having its own photocell 48, a system of mirrors could be adapted to direct both beams to a single photocell. A rotating disc (not shown) which alternatively blocks one beam and allows the other to pass and reach the photocell would allow the single photocell to alternately receive absorption data from each beam to allow the ratio of A/B to be determined. The advantage of using a single photocell is that it would essentially be self-calibrating since the same photocell measures A and B and any drift in the gain of the photocell would cancel out.

In determining the volume of an object placed within the cylinder the absorption values A and B are only important for purposes of determining the ratio of (A/B). The actual unit values of A and B are unimportant, because only a ratio need be determined. Gas concentrations are affected by prevailing atmospheric temperatures and pressures. The relative values A and B are in turn affected, and the apparatus uses transducer 52 and digital thermometer 54 to monitor pressure and temperature. Based upon data received from the thermometer 54 and transducer 52 the computer auto-calibrates, making allowances for changes in optical absorption of first and second laser beams 20, 22 and thereby keeps the relative ratio of A to B consistent, regardless of temperature and pressure changes.

Figure 5:
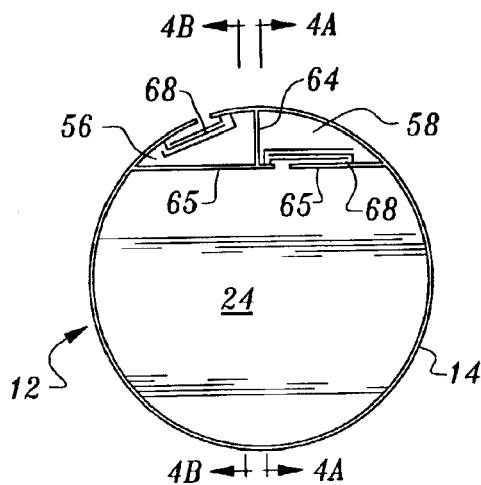
FIG. 5 is an end cutaway view of the cylinder of the apparatus shown in FIGS. 4A, 4B showing a measurement chamber and vented chambers for enclosing first and second laser beams and related components.
Figure 4A:
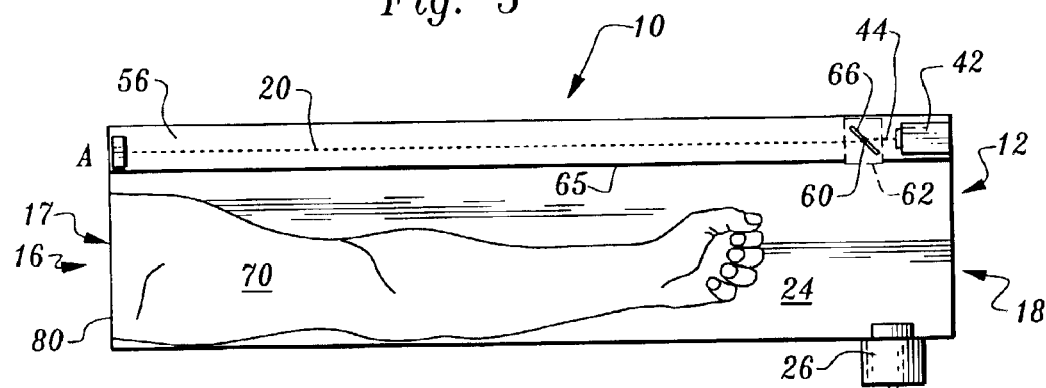
FIG. 4A is a cutaway side view of a second embodiment of the apparatus showing the first and second laser beams and related components located in enclosed chambers; a patient's arm is positioned therein for volume measurement.
Figure 4B:
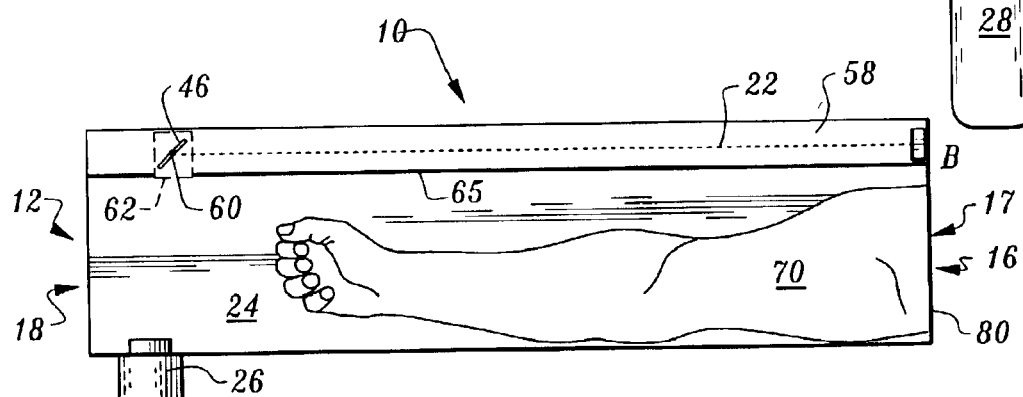
FIG. 4B is an opposite cutaway side view of the embodiment of FIG. 4B.

In addition to barometric pressure effects, the values A and B can be affected by the impingement of stray light upon photocells 48. For this reason, FIGS. 4A, 4B, and 5 show an embodiment of the apparatus where light is all but eliminated along the path length X for first and second beams 20, 22. The projected beam 44 is deflected by the partially silvered mirror 46 and split into first and second beams 20, 22 which are enclosed in their separate chambers 56, 58. The deflected beam 60 travels through a window 62 located in the barrier 64 separating first and second chambers 56, 58 and is deflected from deflecting mirror 66 to become first beam 20. As shown, first beam 20 is enclosed in the first chamber 56 having an attached light baffle 68 that is vented to the outside ambient air. Second beam 22 is enclosed in the second chamber 58 having a light baffle 68 that is vented to a measurement chamber 24 where gas and ambient air are mixed. When a known quantity of gas is injected into the measurement chamber 24, it diffuses throughout measurement chamber 24 and second chamber 58 to reach an equilibrium, at which time optical absorption measurements to derive values A and B are taken. The electronics are designed to make one more gas concentration measurements to detect when the gas reaches equilibrium at which time the computer can be timed to begin taking measurements of values A and B.

The divider 64 between first and second chambers 56, 58, best shown in FIG. 5, runs the entire length of the cylinder 12 and effectively seals first chamber 56 off from any gas present in second chamber 58 and measurement chamber 24. Floor 65 serves as a barrier to guard against objects being placed in the measurement chamber and damaging the mirrors 46, 66, laser projector 42 and photocells 48, upon being lifted out of, or into, the apparatus. This is especially important when the apparatus is used to measure lymphedema in a human limb 70 as shown in the Figures. As shown, floor 65 prevents a patient's arm 70 from lifting and contacting the sensitive elements located in first and second chambers 56, 58.

In addition to values A and B, the determination of gas concentration is dependent on the length X of the path taken by first and second laser beams 20, 22. Path length X is preferably as long as possible. In the drawings path length X is maximized by placing photocell 48 at a furthest point along cylinder 12 from laser projector 42. However, further maximization of path length can occur by including additional deflecting mirrors in first and second chambers (not shown) to deflect first and second beams up and down the cylinder length several more times before reaching photocells. This increased path length X would cause the relative values A and B to be more sensitive to the presence of the gas, thus contributing to better volume determinations.

Ultimately, the objective of the inventive apparatus is to reach a value u which is proportional to gas concentration, which in turn is proportional to the volume of an object placed within the cylinder. The calculation of this value u is as follows:

$$u = 1/x \, Ln(A/B)$$

Where A and B are measured, and X is the known path length. The value u is proportional to gas concentration and changes linearly with the volume of an object. Therefore, when u is determined, so too can the volume of an object be determined.

Figure 6:
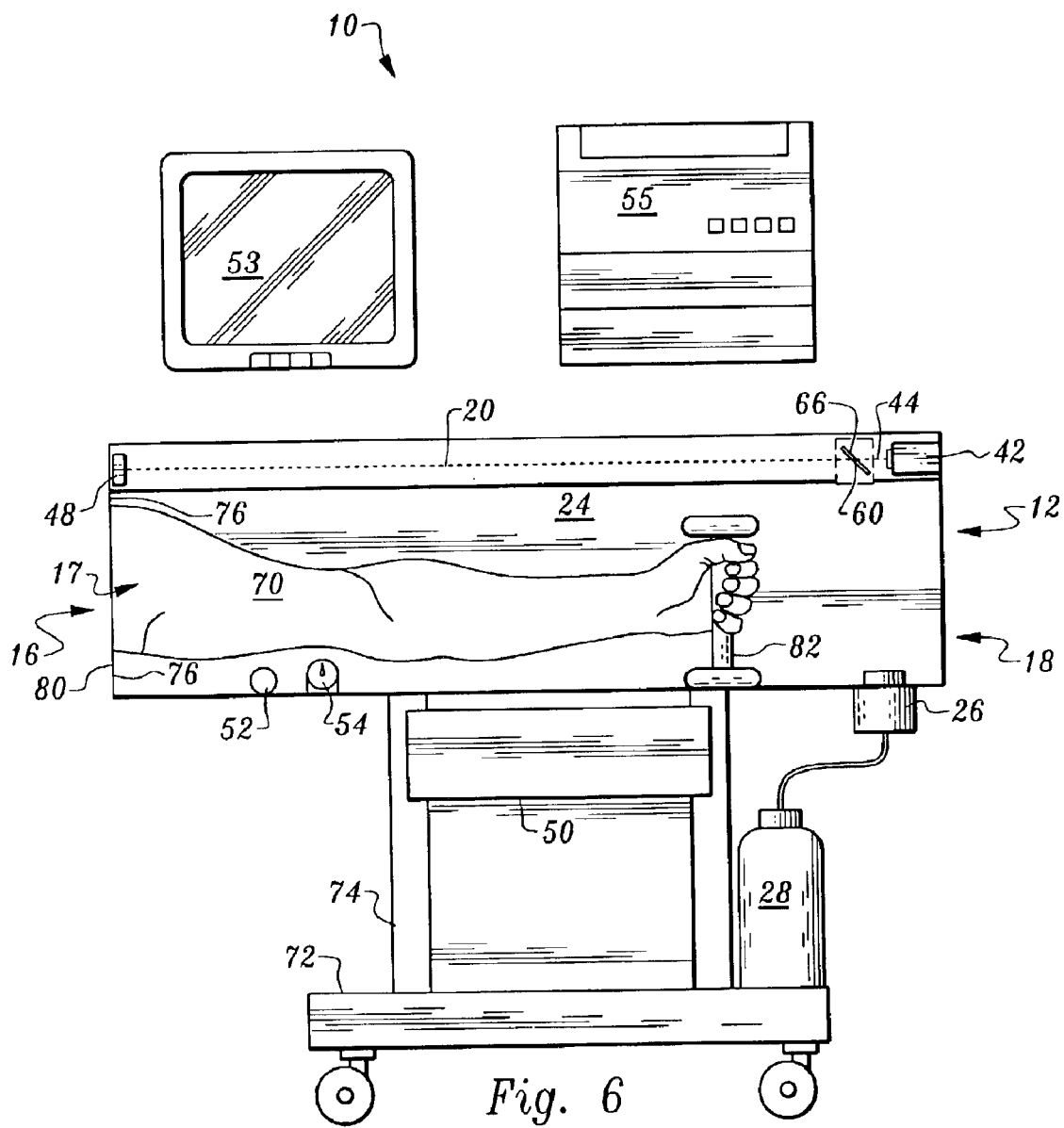
FIG. 6 is a side cutaway view of the second embodiment of the apparatus shown with a patient's arm inserted therein for measuring its volume and having a wheeled stand attached for easy transporting, as well as other peripheral components.

The taking of arm volume measurements is greatly facilitated if the apparatus is portable. As shown in FIG. 6, the apparatus 10 is coupled to a wheeled stand 72 having elevating members 74 for elevating the apparatus 10 to a desired height. This entire apparatus can be easily wheeled about a hospital ward, to take the arm volume measurements of numerous patients. In this way the patient can remain in a hospital bed while the apparatus is wheeled to her to take an arm measurement.

Figure 7:
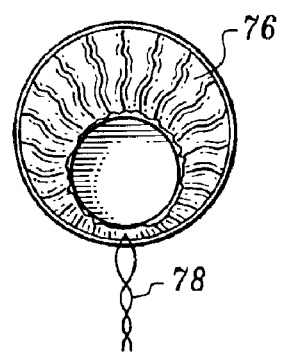
FIG. 7 is a closeup view of the arm insertion sleeve shown in FIG. 6.

FIGS. 6 illustrates a patient's arm 70 placed within the measurement chamber 24 of the cylinder 12. FIG. 7 shows a closeable curtain 76 which is drawn around the upper arm using a draw string or elastic band so that the seal between the curtain 76 and arm 70 is tight, but so the curtain 76 remains planar between the edges 80 of the cylinder 12 and the surface of the patient's arm 70. The curtain's sealing quality is required so as to keep the air-gas mixture from leaking unnecessarily out of the measurement chamber 24 from around a patient's arm 70 while it is inserted therein. A hand hold 82 that is preferably adjustable is placed at a depth within the measurement chamber 24 to allow a patient to grip thereto, and thus maintain a reproducible arm insertion distance into the measurement chamber.

In another embodiment of the invention (not shown), the apparatus serves as both a lymphedema measuring and treating apparatus. In this version, the cylinder 12 is a hardened pressure chamber, where an arm measurement can be taken and if lymphedema is believed to be progressing, the chamber can be pressurized to a therapeutic level until normal arm volume is achieved.

In use for measuring lymphedema, a woman with breast cancer who is going to have surgery including lymph node removal would be measured prior to surgery. Prior to measurement, if the patient has no natural marks, a fiducial mark would be placed on the patient's upper arm (e.g. a small tattoo hash mark in her axilla). The apparatus 10 would be calibrated for temperature and pressure and the arm 70 inserted into the measurement volume 24 up to the fiducial mark. When the fiducial mark is reached, the patient would grip the handhold 82, which can be adjusted for different length arms. The curtain 76 would be drawn around the patient's upper arm and the patient's arm volume would be measured and this measurement would become part of the patient's permanent medical record.

The activation of the volume measurement system first activates the laser 42 (or other light source) and initial readings of the light absorption values A and B are taken several times to determine the stability of the system. The current temperatures and pressures are recorded automatically. Next, the computer activates a small burst of test gas from the cylinder 28. The valve 26 is of the type which precisely regulates the amount of gas released into the cylinder 12. The light absorption values A and B are recorded again, perhaps once, but more likely many individual measurements of A and B are recorded. Optionally, another gas spurt could be released into the cylinder 12, thereby doubling the number of test gas molecules in the measurement chamber 24, and then the absorption values A and B can be measured again to increase the precision for obtaining the value u.

The volume measurement of the patient's arm 70 is displayed on the TV monitor readout 53 and a hard copy of the readout is printed which can be placed in the patient's medical record.

Once the volume determination is completed, the drawstring 78 on the curtain 76 is released and the patient removes her arm 70 from the measurement chamber 24. The curtain can be replaced with another sterile disposable curtain for the next patient.

At points in time after surgery (days, months, or years) the patient can be re-measured using the apparatus, and any differences between this volume and the initial (pre-surgical) volume are a measure of the severity of lymphedema. The fiducial mark remains so that the arm can be inserted into the measurement chamber in a reproducible manner. Incidentally, for long term measurement regimens, (over months or years), the patient's weight should also be measured to make sure that changes in arm volume are not a simple result of weight gain or loss.

If the apparatus is used to measure the volumes of other types of objects, the objects would most likely be placed entirely within the measurement chamber 24 without being connected to something exterior to the volume (e.g. the arm connected to the body). The apparatus 10 might be modified to replace the curtain 76 with a closeable door for the opening to the measurement chamber 24. Otherwise, the apparatus and the measurement procedure would be similar to that noted previously.

Accordingly, the inventive apparatus provides a ready means for measuring the volume of objects and is especially applicable for measuring human limbs to determine the progression of lymphedema.

Finally, although the description above contains many specificities, these should not be construed as limiting the scope of the invention but as merely providing illustrations of some of the presently preferred embodiments of this invention. This invention may be altered and rearranged in numerous ways by one skilled in the art without departing from the scope of the invention.

What is claimed is:

1. An apparatus for measuring differences in light absorption between air and an air-gas mixture, the apparatus comprising:

a rigid housing surrounding a chamber;

an opening in said housing for gaining access to said chamber;

projecting means for projecting a first laser beam through ambient air to a first light detector;

means for introducing a gas into said chamber, said gas mixing with ambient air in said chamber;

projecting means for projecting a second laser beam through said air-gas mixture to a second light detector; and a computer, said computer collecting laser beam absorption data from said first and said second light detectors.

2. The apparatus of claim 1, further comprising a wheeled stand for transporting said apparatus, said wheeled stand supporting said rigid housing.

3. The apparatus of claim 2, wherein said wheeled stand includes at least one elevating member coupled between said wheels and said rigid housing for elevating said rigid housing to a desired height.

4. The apparatus of claim 1, wherein said rigid housing is comprised of an elongate cylinder, a first open end of said cylinder comprising said opening.

5. The apparatus of claim 4, wherein said first and second laser beams are projected from a single projecting means.

6. The apparatus of claim 4, wherein said projecting means is located within said cylinder.

7. The apparatus of claim 5, further comprising a first deflecting mirror positioned in the path of said projecting means for deflecting a beam from said projecting means to a second deflecting mirror, said second mirror deflecting said beam a second time to form said first laser beam.

8. The apparatus of claim 7, wherein said first deflecting mirror is a partially silvered mirror.

9. The apparatus of claim 8, wherein said second light detector receives said second laser beam through said partially silvered mirror.

10. The apparatus of claim 4, further comprising a closure means attached to said cylinder opening, said closure means being sealingly closeable around an object inserted into said closure means.

11. The apparatus of claim 10, wherein said closure means is a sealable curtain.

12. The apparatus of claim 11, wherein said sealable curtain is disposable.

13. The apparatus of claim 1, wherein said gas is selected from the inert gasses.

14. The apparatus of claim 1, wherein said gas is replaced with an aerosol.

15. The apparatus of claim 4, wherein said gas is selected from the inert gasses.

16. An apparatus for measuring differences in light absorption between air and an air-gas mixture, the apparatus comprising:
   a rigid housing surrounding a chamber;
   an opening in said housing for gaining access to said chamber;
   projecting means for projecting light through ambient air to a first light detector;
   means for introducing a gas into said chamber, said gas mixing with ambient air in said chamber;
   projecting means for projecting light through said air-gas mixture to a second light detector; and
   a computer, said computer collecting light absorption data from said first and said second light detectors.

17. The apparatus of claim 16, further comprising a wheeled stand for transporting said apparatus, said wheeled stand supporting said rigid housing.

18. The apparatus of claim 17, wherein said wheeled stand includes at least one elevating member coupled between said wheels and said rigid housing for elevating said rigid housing to a desired height.

19. The apparatus of claim 16, wherein said rigid housing is comprised of an elongate cylinder, a first open end of said cylinder comprising said opening.

20. The apparatus of claim 19, wherein said light is projected from a single projecting means.

21. The apparatus of claim 19, wherein said projecting means is located within said cylinder.

22. The apparatus of claim 19, further comprising a closure means attached to said cylinder opening, said closure means being sealingly closeable around an object inserted into said closure means.

23. The apparatus of claim 22, wherein said closure means is a sealable curtain.

24. The apparatus of claim 23, wherein said sealable curtain is disposable.

25. The apparatus of claim 16, wherein said gas is selected from the inert gasses.

26. The apparatus of claim 16, wherein said gas is replaced with an aerosol.

27. The apparatus of claim 19, wherein said gas is selected from the inert gasses.

28. An apparatus for measuring the volume of an object, comprising:
   a rigid housing surrounding a measurement chamber having a known volume;
   an opening in said housing for gaining access to said chamber and for placing an object therein;
   projecting means for projecting a first laser beam through ambient air to a first light detector;
   means for introducing a gas into said measurement chamber, said gas mixing with ambient air in said chamber;
   projecting means for projecting a second laser beam through said air-gas mixture of said measurement chamber to a second light detector; and
   means for calculating the amount of volume of an object placed within said measurement chamber using the differences in law absorption values derived at said first and second light detectors.

29. An apparatus for measuring differences in laser light absorption between air and a gas, the apparatus comprising:
   a rigid housing surrounding a hollow measurement chamber;
   an opening in said housing for gaining access to said chamber;
   projecting means for projecting a first laser beam through ambient air;
   means for sealing said measurement chamber;
   means for introducing a gas into said sealed measurement chamber, said gas mixing with ambient air in said chamber;
   projecting means for projecting a second laser beam through said air-gas mixture of said measurement chamber; and
   means for collecting laser beam absorption data of said first and second laser beams.

30. An apparatus for measuring differences in light absorption between air and an air-gas mixture, the apparatus comprising:
   a rigid housing surrounding a chamber;
   an opening in said housing for gaining access to said chamber;
   means for projecting a first light beam through ambient air to a first light detector;
   means for introducing a gas into said chamber, said gas mixing with ambient air;
   means for projecting a second light beam through said air-gas mixture to a second light detector; and
   a computer, said computer collecting light beam absorption data from said first and said second light detectors.

31. A method for measuring the volume of an object, comprising:
   providing and activating the apparatus of claim 14;
   placing an object in said chamber of said apparatus; and
   determining a volume measurement of said object by projecting light both through ambient air and through said air-gas mixture.

32. The method of claim 31, further comprising the step of calibrating said apparatus by projecting light through ambient air and through said air-gas mixture when said chamber is empty.

33. The method of claim 31, further comprising the step of calibrating said apparatus by accounting for temperature and pressure changes.

34. The method of claim 31, further comprising the step of pressurizing said chamber to a level where the volume of an object in the chamber decreases.

35. A method for measuring the volume of an animal limb, comprising:
   providing and activating the apparatus of claim 14, wherein said opening in said housing further comprises a sealable closure;
   identifying a fiducial mark on said limb;
   placing said limb in said chamber up to a depth determined by said fiducial mark;
   closing said sealable closure around said limb; and
   determining a volume measurement of said limb by projecting light both through ambient air and through said air-gas mixture.

36. The method of claim 35, further comprising the step of calibrating said apparatus by projecting light through ambient air and through said air-gas mixture when said chamber is empty.

37. The method of claim 35, further comprising the step of calibrating said apparatus by accounting for temperature and pressure changes.

38. An apparatus for measuring differences in light absorption between air and an air-gas mixture, the apparatus comprising:

a rigid housing surrounding a chamber;

an opening in said housing for gaining access to said chamber;

projecting means for projecting a first laser beam through ambient air to a light detector;

means for introducing a gas into said chamber, said gas mixing with ambient air in said chamber;

projecting means for projecting a second laser beam through said air-gas mixture to said light detector; and a computer, said computer collecting laser beam absorption data from said light detector of said first and second laser beams.

39. The apparatus of claim 38, further comprising a wheeled stand for transporting said apparatus, said wheeled stand supporting said rigid housing.

40. The apparatus of claim 39, wherein said wheeled stand includes at least one elevating member coupled between said wheels and said rigid housing for elevating said rigid housing to a desired height.

41. The apparatus of claim 38, wherein said rigid housing is comprised of an elongate cylinder, a first open end of said cylinder comprising said opening.

42. The apparatus of claim 41, wherein said first and second laser beams are projected from a single projecting means.

43. The apparatus of claim 41, wherein said projecting means is located within said cylinder.

44. The apparatus of claim 42, further comprising a first deflecting mirror positioned in the path of said projecting means for deflecting a beam from said projecting means to a second deflecting mirror, said second mirror deflecting said beam a second time to form said first laser beam.

45. The apparatus of claim 44, wherein said first deflecting mirror is a partially silvered mirror.

46. The apparatus of claim 45, wherein said light detector receives said second laser beam through said partially silvered mirror.

47. The apparatus of claim 41, further comprising a closure means attached to said cylinder opening, said closure means being sealingly closeable around an object inserted into said closure means.

48. The apparatus of claim 47, wherein said closure means is a sealable curtain.

49. The apparatus of claim 48, wherein said sealable curtain is disposable.

50. The apparatus of claim 38, wherein said gas is selected from the inert gasses.

51. The apparatus of claim 38, wherein said gas is replaced with an aerosol.

52. The apparatus of claim 41, wherein said gas is selected from the inert gasses.

53. An apparatus for measuring differences in light absorption between air and an air-gas mixture, the apparatus comprising:

a rigid housing surrounding a chamber;

an opening in said housing for gaining access to said chamber;

projecting means for projecting light through ambient air to a light detector;

means for introducing a gas into said chamber, said gas mixing with ambient air in said chamber;

projecting means for projecting light through said air-gas mixture to said light detector; and a computer, said computer collecting light absorption data from said light detector.

54. The apparatus of claim 53, further comprising a wheeled stand for transporting said apparatus, said wheeled stand supporting said rigid housing.

55. The apparatus of claim 54, wherein said wheeled stand includes at least one elevating member coupled between said wheels and said rigid housing for elevating said rigid housing to a desired height.

56. The apparatus of claim 53, wherein said rigid housing is comprised of an elongate cylinder, a first open end of said cylinder comprising said opening.

57. The apparatus of claim 56, wherein said light is projected from a single projecting means.

58. The apparatus of claim 56, wherein said projecting means is located within said cylinder.

59. The apparatus of claim 56, further comprising a closure means attached to said cylinder opening, said closure means being sealingly closeable around an object inserted into said closure means.

60. The apparatus of claim 59, wherein said closure means is a sealable curtain.

61. The apparatus of claim 60, wherein said sealable curtain is disposable.

62. The apparatus of claim 53, wherein said gas is selected from the inert gasses.

63. The apparatus of claim 53, wherein said gas is replaced with an aerosol.

64. The apparatus of claim 56, wherein said gas is selected from the inert gasses.

65. An apparatus for measuring the volume of an object, comprising:

a rigid housing surrounding a measurement chamber having a known volume;

an opening in said housing for gaining access to said chamber and for placing an object therein;

projecting means for projecting a first laser beam through ambient air to a light detector;

means for introducing a gas into said measurement chamber, said gas mixing with ambient air in said chamber;

projecting means for projecting a second laser beam through said air-gas mixture of said measurement chamber to said light detector; and means for calculating the amount of volume of an object placed within said measurement chamber using the differences in laser absorption values derived at said light detector.

66. An apparatus for measuring differences in light absorption between air and an air-gas mixture, the apparatus comprising:

a rigid housing surrounding a chamber;

an opening in said housing for gaining access to said chamber;

means for projecting a first light beam through ambient air to a light detector;

means for introducing a gas into said chamber, said gas mixing with ambient air;

means for projecting a second light beam through said air-gas mixture to said light detector; and a computer, said computer collecting light beam absorption data from said light detector of said first and second light beams.

67. A method for measuring the volume of an object, comprising:

providing and activating the apparatus of claim 51;

placing an object in said chamber of said apparatus; and determining a volume measurement of said object by projecting light both through ambient air and through said air-gas mixture.

68. The method of claim 67, further comprising the step of calibrating said apparatus by projecting light through ambient air and through said air-gas mixture when said chamber is empty.

69. The method of claim 67, further comprising the step of calibrating said apparatus by accounting for temperature and pressure changes.

70. The method of claim 67, further comprising the step of pressurizing said chamber to a level where the volume of an object in the chamber decreases.

71. A method for measuring the volume of an animal limb, comprising:

provessing and activating the apparatus of claim 51, wherein said opening in said housing further comprises a sealable closure;

identifying a fiducial mark on said limb;

placing said limb in said chamber up to a depth determined by said fiducial mark;

closing said sealable closure around said limb; and determining a volume measurement of said limb by projecting light both through ambient air and through said air-gas mixture.

72. The method of claim 71, further comprising the step of calibrating said apparatus by projecting light through ambient air and through said air-gas mixture when said chamber is empty.

73. The method of claim 71, further comprising the step of calibrating said apparatus by accounting for temperature and pressure changes.

* * * * *